US006867328B2

(12) United States Patent
Borgmeier et al.

(10) Patent No.: US 6,867,328 B2
(45) Date of Patent: Mar. 15, 2005

(54) METHOD FOR PRODUCING ACRYLIC ACID BY THE HETEROGENEOUSLY CATALYSED GAS-PHASE OXIDATION OF PROPANE

(75) Inventors: Frieder Borgmeier, Mannheim (DE); Andreas Tenten, Maikammer (DE); Hartmut Hibst, Schriesheim (DE); Klaus Joachim Müller-Engel, Stutensee (DE); Signe Unverricht, Mannheim (DE); Gerhard Cox, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/333,060

(22) PCT Filed: Jul. 16, 2001

(86) PCT No.: PCT/EP01/08178
§ 371 (c)(1),
(2), (4) Date: Jan. 16, 2003

(87) PCT Pub. No.: WO02/06199
PCT Pub. Date: Jan. 24, 2002

(65) Prior Publication Data
US 2003/0187298 A1 Oct. 2, 2003

(30) Foreign Application Priority Data

Jul. 18, 2000 (DE) .......................................... 100 34 825
Sep. 20, 2000 (DE) .......................................... 100 46 672
Apr. 17, 2001 (DE) .......................................... 101 18 814
Apr. 23, 2001 (DE) .......................................... 101 19 933

(51) Int. Cl.[7] ............................................. C07C 57/02
(52) U.S. Cl. ....................... 562/598; 562/542; 562/549; 502/305; 502/311
(58) Field of Search ................................ 562/512, 598, 562/599

(56) References Cited

U.S. PATENT DOCUMENTS

| 5,380,933 A | * | 1/1995 | Ushikubo et al. | ........... 562/549 |
| 6,180,825 B1 | * | 1/2001 | Lin et al. | ..................... 562/549 |
| 6,525,217 B1 | * | 2/2003 | Unverricht et al. | ......... 562/544 |
| 2003/0187299 A1 | * | 10/2003 | Machhammer et al. | ..... 562/547 |

FOREIGN PATENT DOCUMENTS

| DE | 198 35 247 | 2/1999 |
| DE | 100 29 338 | 1/2002 |

(List continued on next page.)

OTHER PUBLICATIONS

Manhua Lin, et al., Reaction Intermediates in the Selective Oxidation of Propane Over a Mixed Metal Oxide Catalyst, Procedings ISO '99, Rimini (Italy), Sep. 10–11, 1999, pp. 143–144.

G. Centi et al.: "In situ Drift study of the reactivity and reaction mechanism of catalysts based on iron–molybdenum oxides encapsulated in boralite for the selective oxidation of alkylaromatics" Catalysis Today, vol. 61, pp. 211–221 2000.

Robert K. Grasselli: "Advances and future trends in selective oxidation and ammoxidation catalysis" Catalysis Today, vol. 49, pp. 141–153 1999.

Hiromu Watanabe et al.: "New synthesis route for Mo–V–Nb–Te mixed oxides catalyst for propane ammoxidation" Applied Catalysis A: General, vol. 194–195, pp. 479–485 2000.

Primary Examiner—Johann Richter
Assistant Examiner—Karl Puttlitz
(74) Attorney, Agent, or Firm—Oblon, Spivak, McClelland, Maier & Neustadt, P.C.

(57) ABSTRACT

The invention relates to a method for producing acrylic acid by the heterogeneously catalysed gas-phase oxidation of propane on a multi-metal oxide mass, said mass containing the elements Mo, V, Te and/or Sb and having a specific X-ray diffractogram.

30 Claims, 6 Drawing Sheets

FOREIGN PATENT DOCUMENTS

| | | | |
|---|---|---|---|
| DE | 100 46 672 | | 3/2002 |
| DE | 101 18 814 | | 10/2002 |
| EP | 0 529 853 | | 3/1993 |
| EP | 0 608 838 | | 8/1994 |
| EP | 0 767 164 | | 4/1997 |
| EP | 0 895 809 | | 2/1999 |
| EP | 0 962 253 | | 12/1999 |
| EP | 1 090 684 | | 4/2001 |
| EP | 1090684 | * | 4/2001 |
| JP | 07053448 | | 2/1995 |
| JP | 07232071 | | 9/1995 |
| JP | 08057319 | | 3/1996 |
| JP | 10-36311 | | 2/1998 |
| JP | 10028862 | | 2/1998 |
| JP | 10057813 | | 3/1998 |
| JP | 10310539 | | 11/1998 |
| JP | 10330343 | | 12/1998 |
| JP | 11042434 | | 2/1999 |
| JP | 11043314 | | 2/1999 |
| JP | 11057479 | | 3/1999 |
| JP | 11169716 | | 6/1999 |
| JP | 11263745 | | 9/1999 |
| JP | 11-285637 | * | 10/1999 |
| JP | 11343261 | | 12/1999 |
| JP | 11343262 | | 12/1999 |
| JP | 2000037623 | | 2/2000 |
| JP | 2000051693 | | 2/2000 |
| WO | 99/03825 | | 1/1999 |
| WO | 00/29105 | | 5/2000 |
| WO | 00/29106 | | 5/2000 |

* cited by examiner

METHOD FOR PRODUCING ACRYLIC ACID BY THE HETEROGENEOUSLY CATALYSED GAS-PHASE OXIDATION OF PROPANE

The present invention relates to a process for the preparation of acrylic acid by heterogeneously catalyzed gas-phase oxidation of propane with molecular oxygen at elevated temperatures over at least one multimetal oxide material of the formula I, $$Mo_1V_bM_c^1M_d^2O_n \qquad (I),$$

where

M$^1$ is Te and/or Sb,

M$^2$ is at least one of the elements from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In, b is from 0.01 to 1, c is from >0 to 1, preferably from 0.01 to 1, d is from >0 to 1, preferably from 0.01 to 1, and n is a number which is determined by the valency and frequency of the elements other than oxygen in (I), whose X-ray diffraction pattern has reflections h, i and k whose peaks are at the diffraction angles (2θ) 22.2±0.4° (h), 27.3±0.4° (i) and 28.2±0.4° (k), the reflection h being the most intense reflection within the X-ray diffraction pattern and having a half-width of not more than 0.5°, the intensity P$_i$ of the reflection i and the intensity P$_k$ of the reflection k fulfilling the relationship 0.65≦R≦0.85, where R is the intensity ratio defined by the formula $$R=P_i/(P_i+P_k)$$

and the half-width of the reflection i and that of the reflection k each being ≦1°.

Multimetal oxide materials which have a stoichiometry corresponding to the formula (I) are known (cf. for example EP-A 608838, EP-A 529853, JP-A 7-232071, JP-A 10-57813, JP-A 2000-37623, JP-A 10-36311, WO 00/29105, Proceedings ISO'99, Rimini (Italy), Sep. 10–11, 1999, G. Centi and S. Perathoner Ed., SCI Pub. 1999, EP-A 767164, Catalysis Today 49 (1999), pages 141–153, EP-A 962253, Applied Catalysis A: General 194 to 195 (2000), pages 479 to 485, JP-A 11/169716, EP-A 895809, DE-A 19835247, DE-A 10029338, JP-A 8-57319, JP-A 10-28862, JP-A 11-43314, JP-A 11-57479, WO 00/29106, JP-A 10-330343, JP-A 11-285637, JP-A 10-310539, JP-A 11-42434, JP-A 11-343261, JP-A 11-343262, WO 99/03825, JP-A 7-53448, JP-A 2000-51693, JP-A 11-263745 and the prior applications DE-A 10046672 and DE-A 10118814).

In the prior art cited, multimetal oxide materials which have a stoichiometry (I) are recommended primarily as catalysts for the heterogeneously catalyzed gas-phase oxidation and/or gas-phase ammoxidation of saturated hydrocarbons to α,β-ethylenically unsaturated carboxylic acids and/or their nitrites (e.g. propane→acrylic acid).

The evaluated prior art also discloses that multimetal oxide materials which have a stoichiometry (I) occur in the form of two crystalline phases which differ from one another and are frequently referred to as i-phase and k-phase (cf. for example JP-A 11-43314, DE-A 10046672 and DE-A 10118814). It is only recent investigations that have led to the discovery that the X-ray diffraction pattern of the two phases has the reflection of strongest intensity at the peak position 2θ=22.2±0.4°. Moreover, the X-ray diffraction pattern of the i-phase, in contrast to the k-phase, contains a reflection with the peak position 2θ=27.3±0.4°, whereas the X-ray diffraction pattern of the k-phase, in contrast to the i-phase, contains a reflection with the peak position 2θ=50.0±0.3°. Both phases additionally have a reflection with the peak position 2θ=28.2±0.4°.

According to WO 00/29106 and WO 00/29105, multimetal oxide materials having the stoichiometry (I) are suitable as catalysts for the heterogeneously catalyzed gas-phase oxidation when they have a substantially amorphous structure which produces an X-ray diffraction pattern in the form of very broad reflections.

In contrast, EP-A 529853 and EP-A 608838 consider it necessary, both for use as catalysts for the heterogeneously catalyzed gas-phase oxidation of propane to acrylic acid and for use as catalysts for the heterogeneously catalyzed gas-phase oxidation of propane to acrylonitrile, for multimetal oxide materials having the stoichiometry (I) to have a specific crystalline structure which produces an X-ray diffraction pattern in the form of very narrow reflections, among which the reflection at the 2θ peak position of 50.0±0.3° is a structurally characteristic main diffraction peak. According to EP-A 529853 and EP-A 608838, further structurally characteristic main diffraction peaks are reflections at the 2θ peak positions of 22.1±0.3°, 28.2±0.3°, 36.2±0.3° and 45.2±0.3°.

In contrast to EP-A 529853 and EP-A 608838, JP-A 11-169716 likewise requires a specific crystalline structure of multimetal oxide materials which likewise appears in the form of very narrow reflections in the X-ray diffraction pattern in order for multimetal oxide materials of the relevant composition to be capable of being put to a corresponding use, but, in addition to the reflections required in EP-A 529853 and in EP-A 608838, JP-A 11-169716 also considers the presence of reflections having 2θ peak positions at 9.0±0.3°, 27.3±0.3°, 29.2±0.3° and 35.4±0.3° in the X-ray diffraction pattern as essential. JP-A 11-169716 considers in particular the simultaneous presence of the two reflections with 2θ peak positions at 28.2±0.3° and 27.3±0.3° with balanced intensity as being necessary for a satisfactory ammoxidation catalyst performance, a sufficient propane conversion being attributed in particular to the reflection having a 2θ peak position at 27.3±0.3° and a satisfactory selectivity of the acrylonitrile formation being attributed in particular to the reflection having a 2θ peak position at 28.2±0.3°.

In Ammoxidation of propane over Mo—V—Nb—Te mixed oxide catalysts from Spillover and Migration of Surface on Catalysts, Ed. by Can Li and Quin Xin, Elsevier Science B. V. (1997), page 473 et seq., the inventors of JP-A 11-169716 furthermore explain that, in their speculative opinion, each of the two abovementioned reflections represents a crystal phase. The multimetal oxide material ideal as a catalyst is said to be a balanced intimate mixture of the two phases, one phase being responsible exclusively for the activation of the propane and the other phase being responsible for a selective conversion of the propane activated over the activating phase into acrylonitrile.

DE-A 19835247 supports the abovementioned view in that it states that the intensities of the X-ray reflections with the 2θ peak positions at 27.3±0.3° and 28.2±0.3° must be within a specific ratio range for a reasonable catalyst performance in the ammoxidation of propane to acrylonitrile.

EP-A 895809, which is a member of the patent family of DE-A 19835247, specifies multimetal oxide materials which have a stoichiometry corresponding to the formula (I) and which are obtainable by processes as also described in DE-A 19835247 as catalysts also suitable for the heterogeneously catalyzed gas-phase oxidation of propane to acrylic acid. The X-ray diffraction pattern of the catalyst in Example 2 of EP-A 895809 has the features according to the claims of this specification.

In comparison, JP-A 7-232071 discloses that substantially only multimetal oxide materials which have the stoichiometry (I) and are present only in the phase represented by the reflection with the 2θ peak position at 27.3±0.3° are also suitable as catalysts for the heterogeneously catalyzed ammoxidation of propane to acrylonitrile.

JP-A 8-57319 discloses that Mo- and/or V-containing multimetal oxide materials can be activated by treatment with acid.

According to EP-A 1090684, multimetal oxide materials I suitable for the catalytic gas-phase oxidation of propane to acrylic acid have a reflection at the peak position 2θ=50.0°.

It is an object of the present invention, in view of the abovementioned prior art, to provide a process for the preparation of acrylic acid by heterogeneously catalyzed gas-phase oxidation of propane with molecular oxygen at elevated temperatures over a multimetal oxide material as defined at the outset and of the formula (I), which shows that these multimetal oxide materials neither need be amorphous nor need contain fractions of a second phase in order to be suitable as catalysts for the heterogeneously catalyzed gas-phase oxidation of propane with molecular oxygen at elevated temperatures to acrylic acid.

We have found that this object is achieved by a process for the preparation of acrylic acid by heterogeneously catalyzed gas-phase oxidation of propane with molecular oxygen at elevated temperatures over at least one multimetal oxide material of the formula I $$Mo_1V_bM_c^1M_d^2O_n \qquad (I),$$

where

M$^1$ is Te and/or Sb,

M$^2$ is at least one of the elements from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In, b is from 0.01 to 1, c is from >0 to 1, preferably from 0.01 to 1, d is from >0 to 1, preferably from 0.01 to 1, and n is a number which is determined by the valency and frequency of the elements other than oxygen in (I), whose X-ray diffraction pattern has reflections h, i and k whose peaks are at the diffraction angles (2θ) 22.2±0.4° (h), 27.3±0.4° (i) and 28.2±0.4° (k), the reflection h being the most intense reflection within the X-ray diffraction pattern and having a half-width of not more than 0.5°, the intensity $P_i$ of the reflection i and the intensity $P_k$ of the reflection k fulfilling the relationship 0.65≦R≦0.85, where R is the intensity ratio defined by the formula $$R=P_i/(P_i+P_k)$$

and the half-width of the reflection i and that of the reflection k each being ≦1°, the at least one multimetal oxide material (I) is one whose X-ray diffraction pattern has no reflection with the peak position 2θ=50.1±0.3°, i.e., is one which contains no k-phase.

The significance of the absence of the abovementioned reflection as evidence for the absence of k-phase had not yet been recognized in the prior application DE-A 10046672.

Rather, the magnitude of the ratio R was regarded as substantially the only indicator of the phase composition. However, very recent results of investigations have shown that R can vary within a certain range even when pure i-phase is present.

According to the invention, preferably 0.67≦R≦0.75 and very particularly preferably R is from 0.70 to 0.75 or R is 0.72.

Surprisingly, it has been found that the multimetal oxide materials (I) to be used according to the invention have higher activity for the novel process and also result in higher selectivity with respect to the acrylic acid formation.

According to the invention, the use of multimetal oxide materials (I) where M$^1$ is Te is preferred. Furthermore, multimetal oxide materials (I) which are advantageous for the novel process are those in which M$^2$ is Nb, Ta, W and/or Ti. Preferably, M$^2$ is Nb. The stoichiometric coefficient b of the multimetal oxide active materials (I) to be used according to the invention is advantageously from 0.1 to 0.6. In a corresponding manner, the preferred range of the stoichiometric coefficient c is from 0.01 to 1 or from 0.05 to 0.4, and advantageous values of d are from 0.01 to 1 or from 0.1 to 0.6. Particularly advantageous multimetal oxide materials (I) to be used according to the invention are those in which the stoichiometric coefficients b, c and d are simultaneously in the abovementioned preferred ranges. Further stoichiometries suitable according to the invention are those disclosed in the publications of the prior art cited at the outset, in particular in JP-A 7-53448.

A specific process for the preparation of multimetal oxide materials (I) to be used according to the invention is disclosed, for example, in JP-A 11-43314 and the prior application DE-A 10118814, in which the relevant multimetal oxide materials (I) are recommended as catalysts for the heterogeneously catalyzed oxydehydrogenation of ethane to ethylene and as catalysts for the heterogeneously catalyzed gas-phase oxidation of propene to acrylic acid.

Accordingly, in a manner known per se and disclosed in most of the prior art publications cited (for example, also as described in the prior application DE-A 10033121), a multimetal oxide material having the stoichiometry (I), which is a mixture of i-phase and other phases (e.g. k-phase), is first produced. In this mixture, the proportion of i-phase can then be increased, for example, by removing the other phases, for example the k-phase, under the microscope or by washing the multimetal oxide material with suitable liquids. Suitable liquids of this type are, for example, aqueous solutions of organic acids, (for example oxalic acid, formic acid, acetic acid, citric acid and tartaric acid), inorganic acids (for example nitric acid), alcohols and aqueous hydrogen proxide [sic] solutions. Furthermore, JP-A 7-232071 also discloses a process for the preparation of multimetal oxide materials (I) to be used according to the invention.

In a less systematic manner, multimetal oxide materials (I) to be used according to the invention are obtainable by the preparation method published in DE-A 19835247. According to this, a very intimate, preferably finely divided, dry blend is produced from suitable sources of their elemental constituents and said dry blend is treated thermally at from 350 to 700° C. or from 400 to 650° C. or from 400 to 600° C. The thermal treatment can in principle be carried out under an oxidizing, reducing or inert atmosphere. A suitable oxidizing atmosphere is, for example, air, air enriched with molecular oxygen or air depleted in oxygen. Preferably, the thermal treatment is carried out under an inert atmosphere, for example under molecular nitrogen and/or noble gas. Usually, the thermal treatment is effected at atmospheric pressure (1 atm). Of course, the thermal treatment can also be carried out under reduced or superatmospheric pressure.

If the thermal treatment is carried out under a gaseous atmosphere, this may be either stationary or flowing. Altogether, the thermal treatment may take up to 24 hours or more.

The thermal treatment is preferably first carried out under an oxidizing (oxygen-containing) atmosphere (e.g. under air) at from 150 to 400° C. or from 250 to 350° C. Thereafter, the thermal treatment is expediently continued under an inert gas at from 350 to 700° C. or from 400 to 650° C. or from 400 to 600° C. Of course, the thermal treatment can also be effected in a manner such that the catalyst precursor material is first tableted (if required after being powdered and, if required, with addition of from 0.5 to 2% by weight of finely divided graphite) before its thermal treatment and then subjected to the thermal treatment and subsequently converted into chips.

The thorough mixing of the starting compounds in the preparation of multimetal oxide materials (I) to be used according to the invention can be effected in dry or in wet form. If it is effected in dry form, the starting compounds are expediently used in the form of finely divided powders and are subjected to the calcination (thermal treatment) after mixing and, if required, compaction.

Preferably, however, the thorough mixing is effected in wet form. Usually, the starting compounds are mixed with one another in the form of an aqueous solution and/or suspension. The aqueous material is then dried and is calcined after drying. Expediently, the aqueous material is an aqueous solution or an aqueous suspension. Preferably, the drying process is carried out immediately after the preparation of the aqueous mixture by spray-drying (the outlet temperatures are as a rule from 100 to 150° C.; the spray-drying can be carried out by the cocurrent or countercurrent method), which requires a particularly intimate dry blend, especially when the aqueous material to be spray-dried is an aqueous solution or suspension.

Suitable sources of the elemental constituents for carrying out the above-described method for the preparation of the multimetal oxide materials (I) to be used according to the invention are all those which are capable of forming oxides and/or hydroxides on heating (if necessary in air). Of course, oxides and/or hydroxides of the elemental constituents can themselves be concomitantly or exclusively used as such starting compounds.

Sources of the element Mo which are suitable according to the invention are, for example, molybdenum oxides, such as molybdenum trioxide, molybdates, such as ammonium heptamolybdate tetrahydrate and molybdenum halides, such as molybdenum chloride.

Suitable starting compounds of the element V which are to be concomitantly used according to the invention are, for example, vanadyl acetylacetonate, vanadates, such as ammonium metavanadate, vanadium oxides, such as vanadium pentoxide ($V_2O_5$), vanadium halides, such as vanadium tetrachloride ($VCl_4$), and vanadium oxyhalides, such as $VOCl_3$. Other vanadium starting compounds which may be concomitantly used are those which contain the vanadium in the oxidation state +4.

According to the invention, suitable sources of the element tellurium are tellurium oxides, such as tellurium dioxide, metallic tellurium, tellurium halides, such as $TeCl_2$, and also telluric acids, such as orthothelluric [sic] acid $H_6TeO_6$.

Advantageous antimony starting compounds are antimony halides, such as $SbCl_3$, antimony oxides, such as antimony trioxide ($Sb_2O_3$), antimonic acids, such as $HSb(OH)_6$, and also antimony oxide salts, such as antimony oxide sulfate $(SbO)_2SO_4$.

Niobium sources suitable according to the invention are, for example, niobium oxides, such as niobium pentoxide ($Nb_2O_5$), niobium oxyhalides, such as $NbOCl_3$, niobium halides, such as $NbCl_5$, and also complex compounds of niobium and organic carboxylic acids and/or dicarboxylic acids, e.g. oxalates and alcoholates. The Nb-containing solutions used in EP-A 895 809 are of course also suitable as a niobium source.

Regarding all other possible elements $M^2$, their halides, nitrates, formates, oxalates, acetates, carbonates and/or hydroxides, are starting compounds which are particularly suitable according to the invention. Suitable starting compounds are often also their oxo compounds, such as tungstates or the acids derived therefrom. Frequently, ammonium salts, too, are used as starting compounds.

Other suitable starting compounds for the preparation of the novel multimetal oxide materials (I) are polyanions of the Anderson type, as described, for example, in Polyhedron 6, No. 2 (1987), 213–218. A further suitable literature source for polyanions of the Anderson type is Kinetics and Catalysis 40, No. 3 (1999), 401 to 404.

Other polyanions suitable as starting compounds are, for example, those of the Dawson or Keggin type. Starting compounds which are preferably used according to the invention are those which are converted into their oxides at elevated temperatures, either in the presence or in the absence of oxygen, possibly with liberation of gaseous compounds.

The multimetal oxide materials (I) obtainable as described and to be used according to the invention can be used as such [for example as powder or after tableting of the powder (frequently with addition of from 0.5 to 2% by weight of finely divided graphite) and subsequent conversion into chips] or in the form of moldings for the novel process. The catalyst bed may be a fixed bed, a moving bed or a fluidized bed.

The shaping to give moldings can be effected, for example, by application to a support, as described in the prior application DE-A 10051419.

The supports to be used for the multimetal oxide materials (I) to be used according to the invention are preferably chemically inert, i.e. they substantially do not participate in the course of the catalytic gas-phase oxidation of propane to acrylic acid, which is catalyzed by the multimetal oxide active materials to be used according to the invention.

According to the invention, particularly suitable materials for the supports are alumina, silica, silicates, such as clay, kaolin, steatite, pumice, aluminum silicate and magnesium silicate, silicon carbide, zirconium dioxide and thorium dioxide.

The surface of the support may be either smooth or rough. Advantageously, the surface of the support is rough since pronounced surface roughness generally results in greater adhesive strength of the active material coat applied.

Frequently, the surface roughness $R_z$ of the support is from 5 to 200 $\mu$m, often from 20 to 100 $\mu$m (determined according to DIN 4768, Sheet 1, using a Hommel tester for DIN-ISO measured surface variables, from Hommelwerke, Germany).

Furthermore, the support material may be porous or nonporous. The support material is expediently nonporous (total volume of the pores $\leq$1% by volume, based on the volume of the support).

The thickness of the active oxide material coat present on the novel coated catalysts is usually from 10 to 1000 μm. However, it may also be from 50 to 700 μm, from 100 to 600 μm or from 150 to 400 μm. Other possible coat thicknesses are from 10 to 500 μm, from 100 to 500 μm or from 150 to 300 μm.

In principle, any desired geometries of the supports are suitable for the novel process. Their longest dimension is as a rule from 1 to 10 mm. However, spheres or cylinders, in particular hollow cylinders, are preferably used as supports. Advantageous diameters for spherical supports are from 1.5 to 4 mm. If cylinders are used as supports, their length is preferably from 2 to 10 mm and their external diameter preferably from 4 to 10 mm. In the case of rings, the wall thickness is moreover usually from 1 to 4 mm. Annular supports suitable according to the invention may also have a length of from 3 to 6 mm, an external diameter of from 4 to 8 mm and a wall thickness of from 1 to 2 mm. However, a support ring geometry of 7 mm×3 mm×4 mm or of 5 mm×3 mm×2 mm (external diameter×length×internal diameter) is also possible.

The preparation of coated catalysts to be used according to the invention can be carried out in a very simple manner by preforming oxide materials to be used according to the invention and of the formula (I), converting them into a finely divided form and finally applying them to the surface of the support with the aid of a liquid binder. For this purpose, the surface of the support is moistened in a very simple manner with the liquid binder, and a coat of the active material is caused to adhere to the moistened surface by bringing into contact with finely divided active oxide material of the formula (I). Finally, the coated support is dried. of course, the process can be repeated periodically in order to obtain a greater coat thickness. In this case, the coated parent body becomes a new support, etc.

The fineness of the catalytically active oxide material of the formula (I) which is to be applied to the surface of the support is of course adapted to the desired coat thickness. For the coat thickness range from 100 to 500 μm, suitable active material powders are, for example, those in which at least 50% of the total number of powder particles pass through a sieve of mesh size from 1 to 20 μm and whose numerical proportion of particles having a longest dimension above 50 μm is less than 10%. As a rule, the distribution of the longest dimensions of the powder particles corresponds to a Gaussian distribution as a result of the preparation. Frequently, the particle size distribution is as follows:

a rule $\geq 0°$ and $\leq 90°$, generally $\geq 30°$ and $\leq 90°$; the angle of inclination is the angle of the central axis of the rotating container relative to the horizontal) rotating container (for example a rotating pan or coating drum). The rotating container transports the supports, which, for example, are spherical or cylindrical, under two metering apparatuses arranged a specific distance apart. The first of the two metering apparatuses expediently corresponds to a nozzle (for example an atomizer nozzle operated using compressed air), through which the supports rolling in the rotating pan are sprayed with the liquid binder and moistened in a controlled manner. The second metering apparatus is located outside the atomization cone of the liquid binder sprayed in and serves for supplying the finely divided oxidic active material (for example via a vibrating conveyor or a powder screw). The support spheres moistened in a controlled manner take up the active material powder supplied which is compacted into a cohesive coat by the rolling movement on the outer surface of the support, which, for example, is cylindrical or spherical.

If required, the support thus provided with a base coat passes through the spray nozzles again in the course of the subsequent revolution and is moistened thereby in a controlled manner in order to be able to take up a further coat of finely divided oxidic active material in the course of further movement, etc. (intermediate drying is as a rule not necessary). Finely divided oxidic active material and liquid binder are generally fed in continuously and simultaneously.

The removal of the liquid binder can be effected after coating is complete, for example by the action of hot gases, such as $N_2$ or air. It is noteworthy that the coating process described results in both completely satisfactory adhesion of the successive coats to one another and of the base coat to the surface of the support.

What is important for the coating method described above is that the moistening of the support surface to be coated is carried out in a controlled manner. Briefly, this means that the support surface is expediently moistened in such a way that it has adsorbed liquid binder but no liquid phase as such is visible on the support surface. If the support surface is too moist, the finely divided catalytically active oxide material agglomerates into separate agglomerates instead of being adsorbed onto the surface. Detailed information in this context is to be found in DE-A 2909671 and DE-A 10051419.

The abovementioned final removal of the liquid binder used can be carried out in a controlled manner, for example

| D (μm) | 1 | 1.5 | 2 | 3 | 4 | 6 | 8 | 12 | 16 | 24 | 32 | 48 | 64 | 96 | 128 |
|---|---|---|---|---|---|---|---|---|---|---|---|---|---|---|---|
| x | 80.5 | 76.3 | 67.1 | 53.4 | 41.6 | 31.7 | 23 | 13.1 | 10.8 | 7.7 | 4 | 2.1 | 2 | 0 | 0 |
| y | 19.5 | 23.7 | 32.9 | 46.6 | 58.4 | 68.3 | 77 | 86.9 | 89.2 | 92.3 | 96 | 97.9 | 98 | 100 | 100 |

Here:

D=diameter of the particle, x=the percentage of the particles whose diameter is $\geq D$ and y=the percentage of the particles whose diameter is <D.

In order to carry out the coating process described on an industrial scale, it is advisable, for example, to use the principle disclosed in DE-A 2909671 and that disclosed in DE-A 10051419, i.e. the supports to be coated are initially taken in a preferably inclined (the angle of inclination is as by evaporation and/or sublimation. In the simplest case, this can be effected by the action of hot gases of corresponding temperature (frequently from 50 to 300° C., often 150° C.). However, it is possible to effect only preliminary drying by the action of hot gases. The final drying can then be carried out, for example, in a drying oven of any desired type (for example a belt drier) or in the reactor. The temperature acting should not be above the calcination temperature used for the preparation of the oxidic active material. Of course, the drying can also be carried out exclusively in a drying oven.

Regardless of the type and geometry of the support, the following may be used as binders for the coating process: water, monohydric alcohols, such as ethanol, methanol, propanol and butanol, polyhydric alcohols, such as ethylene glycol, 1,4-butanediol, 1,6-hexanediol or glycerol, monobasic or polybasic organic carboxylic acids, such as propionic acid, oxalic acid, malonic acid, glutaric acid or maleic acid, amino alcohols, such as ethanolamine or diethanolamine, and monofunctional or polyfunctional organic amides, such as formamide. Other advantageous binders are solutions consisting of from 20 to 90% by weight of water and from 10 to 80% by weight of an organic compound which is dissolved in water and whose boiling point or sublimation temperature at atmospheric pressure (1 atm) is >100° C., preferably >150° C. Advantageously, the organic compound is selected from the above list of possible organic binders. The organic content of abovementioned aqueous binder solutions is preferably from 10 to 50, particularly preferably from 20 to 30, % by weight. Other suitable organic components are monosaccharides and oligosaccharides, such as glucose, fructose, sucrose or lactose, and polyethylene oxides and polyacrylates.

What is important is that the preparation of coated catalysts suitable according to the invention can be carried out not only by application of the prepared, finely milled active oxide materials of the formula (I) to the moistened support surface.

Rather, instead of the active oxide material, a finely divided precursor material thereof can also be applied to the moistened support surface (using the same coating process and binder) and the calcination can be carried out after drying of the coated support.

A suitable finely divided precursor material of this type is, for example, that material which is obtainable by first producing a very intimate, preferably finely divided, dry blend from the sources of the elemental constituents of the desired active oxide material of the formula (I) (for example by spray-drying an aqueous suspension or solution of the sources) and subjecting this finely divided dry blend (if necessary after tableting with addition of from 0.5 to 2% by weight of finely divided graphite) to a thermal treatment at from 150 to 350° C., preferably 250 to 350° C., under an oxidizing (oxygen-containing) atmosphere (e.g. under air) for a few hours and finally subjecting it, if required, to milling.

After the coating of the supports with the precursor material, calcination is then preferably carried out under an inert gas atmosphere (all other atmospheres are also suitable) at from 360 to 700° C. or from 400 to 650° C. or from 400 to 600° C.

Of course, the shaping of multimetal oxide materials (I) which may be used according to the invention can also be carried out by extrusion and/or tableting of both finely divided multimetal oxide material (I) and finely divided precursor material of a multimetal oxide material (I).

Suitable geometries are spheres, solid cylinders and hollow cylinders (rings). The longest dimension of the abovementioned geometries is as a rule from 1 to 10 mm. In the case of cylinders, their length is preferably from 2 to 10 mm and their external diameter preferably from 4 to 10 mm. In the case of rings, the wall thickness is moreover usually from 1 to 4 mm. Annular unsupported catalysts suitable according to the invention may also have a length of from 3 to 6 mm, an external diameter of from 4 to 8 mm and a wall thickness of from 1 to 2 mm. However, an unsupported catalyst in annular form may also have a geometry of 7 mm×3 mm×4 mm or of 5 mm×3 mm×2 mm (external diameter×length×internal diameter).

For the novel process, suitable geometries of the multimetal oxide active materials (I) to be used are of course also all those in DE-A 10101695.

According to the invention, it is important that the multimetal oxide materials (I) to be used according to the invention have an X-ray diffraction pattern (always based on $CuK_\alpha$ radiation in this document) which has reflections h, i and k whose peaks are at the diffraction angles (2θ) 22.2±0.4° (h), 27.3±0.4° (i) and 28.2±0.4° (k), the reflection h being the most intense reflection within the X-ray diffraction pattern and having a half-width of not more than 0.5°, the intensity $P_i$ of the reflection i and the intensity $P_k$ of the reflection k fulfilling the relationship 0.65≦R≦0.85, where R is the intensity ratio defined by the formula $$R=P_i/(P_i+P_k)$$

and the half-width of the reflection i and that of the reflection k each being ≦1°.

At the same time, the X-ray diffraction pattern should have no reflection with the peak position 2θ=50.0±0.3°.

In this document, the definition of the intensity of a reflection in the X-ray diffraction pattern is based on the definition set out in DE-A 19835247 and that in DE-A 10051419 and DE-A 10046672.

This means that, if $A^1$ is the peak of a reflection 1 and $B^1$ is the nearest pronounced minimum (minima having reflection shoulders are not taken into account) to the left of the peak $A^1$, in the line of the X-ray diffraction pattern when viewed along the intensity axis perpendicular to the 2θ axis, and, in a corresponding manner, $B^2$ is the nearest pronounced minimum to the right of the peak $A^1$ and $C^1$ is the point at which a straight line drawn from the peak $A^1$ perpendicular to the 2θ axis intersects a straight line connecting the points $B^1$ and $B^2$, then the intensity of the reflection 1 is the length of the linear intercept $A^1C^1$ which extends from the peak $A^1$ to the point $C^1$. The expression minimum denotes a point at which the slope of a tangent to the curve in a base region of the reflection 1 changes from a negative value to a positive value or a point at which the slope tends to zero, the coordinates of the 2θ axis and of the intensity axis being used for specifying the slope.

In this document, the half-width is, in a corresponding manner, the length of the linear intercept between the two intersection points $H^1$ and $H^2$ if a line parallel to the 2θ axis is drawn in the middle of the linear intercept $A^1C^1$, where $H^1$ and $H^2$ are the respective first intersection point of this parallel line with the line, as defined above, of the X-ray diffraction pattern to the left and right of $A^1$.

An exemplary procedure for determining half-width and intensity is also shown in FIG. 6 in DE-A 10046672.

In addition to reflections h, i and k, the X-ray diffraction pattern of the advantageous multimetal oxide materials (I) to be used according to the invention also contains, as a rule, further reflections whose peaks are at the following diffraction angles (2θ):

9.0±0.4° (l), 6.7±0.4° (o)

and 7.9±0.4° (p).

It is advantageous if the X-ray diffraction pattern of the catalytically active oxide materials of the formula (I) additionally contains a reflection whose peaks is [sic] at the following diffraction angle (2θ):

45.2±0.4° (q).

Frequently, the X-ray diffraction pattern of multimetal oxide active materials (I) also contains the reflections 29.2±0.4° (m) and 35.4±0.4° (n).

If the intensity 100 is assigned to the reflection h, it is advantageous according to the invention if the reflections i, l, m, n, o, p and q have the following intensities on the same intensity scale:

i: from 5 to 95, frequently from 5 to 80, in some cases from 10 to 60;

l: from 1 to 30;

m: from 1 to 40;

n: from 1 to 40;

o: from 1 to 30;

p: from 1 to 30 and q: from 5 to 60.

If the X-ray diffraction pattern contains any of the above-mentioned additional reflections, the half-width thereof is as a rule ≦1°.

All data in this document which are based on an X-ray diffraction pattern relate to an X-ray diffraction pattern produced using Cu-Kα radiation (Siemens diffractometer Theta-Theta D-5000, tube voltage: 40 kV, tube current: 40 mA, aperture V20 (variable), collimator V20 (variable), secondary monochromator (0.1 mm), detector aperture (0.6 mm), measuring interval (2θ): 0.02°, measuring time per step: 2.4 s, detector: scintillation counter).

The specific surface area of multimetal oxide materials (I) to be used according to the invention is often from 1 to 30 m$^2$/g (BET surface area, nitrogen).

Otherwise, the novel process can be carried out in the same way as the procedures described in EP-A 608838, WO 00/29106 and JP-A 10-36311. For example, air, air enriched with oxygen or depleted in oxygen or pure oxygen may be used as a source of the required molecular oxygen.

The novel process is advantageous particularly when the reaction gas starting mixture contains no noble gas, in particular no helium, as inert diluent gas. Otherwise, the reaction gas starting mixture may of course comprise inert diluent gases, e.g. N$_2$, CO and CO$_2$, in addition to propane and molecular oxygen. Steam as a component of the reaction gas mixture is advantageous according to the invention.

This means that the reaction gas starting mixture with which the novel multimetal oxide active material is to be loaded at reaction temperatures of, for example, from 200 to 550° C. or from 230 to 480° C. or from 300 to 440° C. may have, for example, the following composition:

from 1 to 15, preferably from 1 to 7, % by volume of propane, from 44 to 99% by volume of air and from 0 to 55% by volume of steam.

Steam-containing reaction gas starting mixtures are preferred.

Other possible compositions of the reaction gas starting mixture are:

from 70 to 95% by volume of propane, from 5 to 30% by volume of molecular oxygen and from 0 to 25% by volume of steam.

Of course, a product gas mixture which does not consist exclusively of acrylic acid is obtained in the novel process. Rather, in addition to unconverted propane, the product gas mixture contains secondary components, such as propene, acrolein, CO$_2$, CO, H$_2$O, acetic acid, propionic acid, etc., from which the acrylic acid must be separated off.

This can be effected in the manner known from the heterogeneously catalyzed gas-phase oxidation of propene to acrylic acid.

This means that the acrylic acid present can be taken up from the product gas mixture by absorption with water or by absorption with a high-boiling inert hydrophobic organic solvent (for example a mixture of diphenyl ether and diphyl, which may also contain additives, such as dimethyl phthalate). The resulting mixture of absorbent and acrylic acid can then be worked up in a manner known per se by rectification, extraction and/or crystallization to give the pure acrylic acid. Alternatively, the basic separation of the acrylic acid from the product gas mixture can also be effected by fractional condensation, as described, for example, in DE-A 19 924 532.

The resulting aqueous acrylic acid condensate can then be further purified, for example, by fractional crystallization (for example suspension crystallization and/or layer crystallization).

The residual gas mixture remaining during the basic separation of the acrylic acid contains in particular unconverted propane. This can be separated from the residual gas mixture, for example by fractional rectification under superatmospheric pressure, and then recycled to the novel gas-phase oxidation. However, it is more advantageous to bring the residual gas into contact (for example by passing it through) with a hydrophobic organic solvent capable of preferentially absorbing the propane, in an extraction apparatus.

By subsequent desorption and/or stripping with air, the absorbed propane can be liberated again and can be recycled to the novel process. In this way, economical overall propane conversions can be achieved. Propene formed as a secondary component is as a rule not separated from the propane and is circulated with it.

It is surprising according to the invention that, with the use of multimetal oxide materials to be used according to the invention and having the stoichiometry (I) as catalysts for the gas-phase catalytic oxidation of propane to acrylic acid, the i-phase and not the k-phase and not a simultaneous presence of i-phase and k-phase is of decisive importance, in contrast to the opinion held in the prior art. What is also unexpected is that, when used as catalysts for the heterogeneously catalyzed gas-phase oxidation of propane to acrylic acid, multimetal oxide materials (I) present in the i-phase have higher activity than if they are present in the k-phase. The higher selectivity with respect to the acrylic acid formation is also surprising.

Furthermore surprising is that the multimetal oxide materials (I) to be used according to the invention have satisfactory stability when they are used as catalysts for the heterogeneously catalyzed gas-phase oxidations of propane to acrylic acid.

Of course, the multimetal oxide materials (I) to be used according to the invention can also be used in the novel process in a form diluted with finely divided, for example colloidal, materials, such as silica, titanium dioxide, alumina, zirconium oxide or niobium oxide.

The dilution mass ratio may be up to 9 (diluent):1 (active material), i.e. possible dilution mass ratios are, for example, 6 (diluent):1 (active material) and 3 (diluent):1 (active material). The diluents can be incorporated before and/or after the calcination. If the incorporation is effected before the calcination, the diluent must be chosen so that it is substantially retained as such during the calcination. This is generally true, for example, in the case of oxides calcinated at correspondingly high temperatures.

The multimetal oxide materials to be used according to the invention are also suitable as catalysts for the gas-phase catalytic oxidative preparation of methacrylic acid from its $C_4$ precursors, e.g. n-butane or isobutane.

The multimetal oxide materials (I) to be used according to the invention are also suitable for the gas-phase catalytic oxidation of acrolein and of propene to acrylic acid and of methacrolein and other $C_4$ precursors, e.g. isobutene or isobutane, to methacrylic acid. Of course, they are also suitable for gas-phase catalytic ammoxidation of propene and/or propane to acrylonitrile. Catalysts consumed in the novel process can be regenerated repeatedly by loading with oxygen-containing gases, for example air or air depleted in oxygen or enriched with oxygen, to which steam may also have been added, at temperatures ≦ reaction temperature.

EXAMPLES

A) Preparation of Catalysts a) Comparison 1. 706.2 g of ammonium heptamolybdate hydrate having an $MoO_3$ content of 81.53% by weight (ideal composition: $(NH_4)_6Mo_7O_{24} \cdot 4H_2O$, from Starck) were dissolved, with stirring, in 6000 ml of water which was at 80° C. While maintaining the 80° C., first 141.0 g of ammonium metavanadate ($V_2O_5$ content of 77.4% by weight, ideal composition: $NH_4VO_3$, from G. f. E. Nürnberg) and then 211.28 g of telluric acid (99% by weight of $H_6TeO_6$, from Fluka) were added in succession, with further stirring, to the resulting clear colorless solution. A solution A was obtained. The solution A was allowed to cool to 30° C. An aqueous niobium oxalate solution consisting of 221.28 g of niobium oxalate (from H. C. Starck, Goslar, Germany, Nb content=20.1% by weight) and 2000 ml of water at 30° C. was added, with further stirring and while maintaining the 30° C., to the clear red solution A cooled to 30° C.

Figure 1:
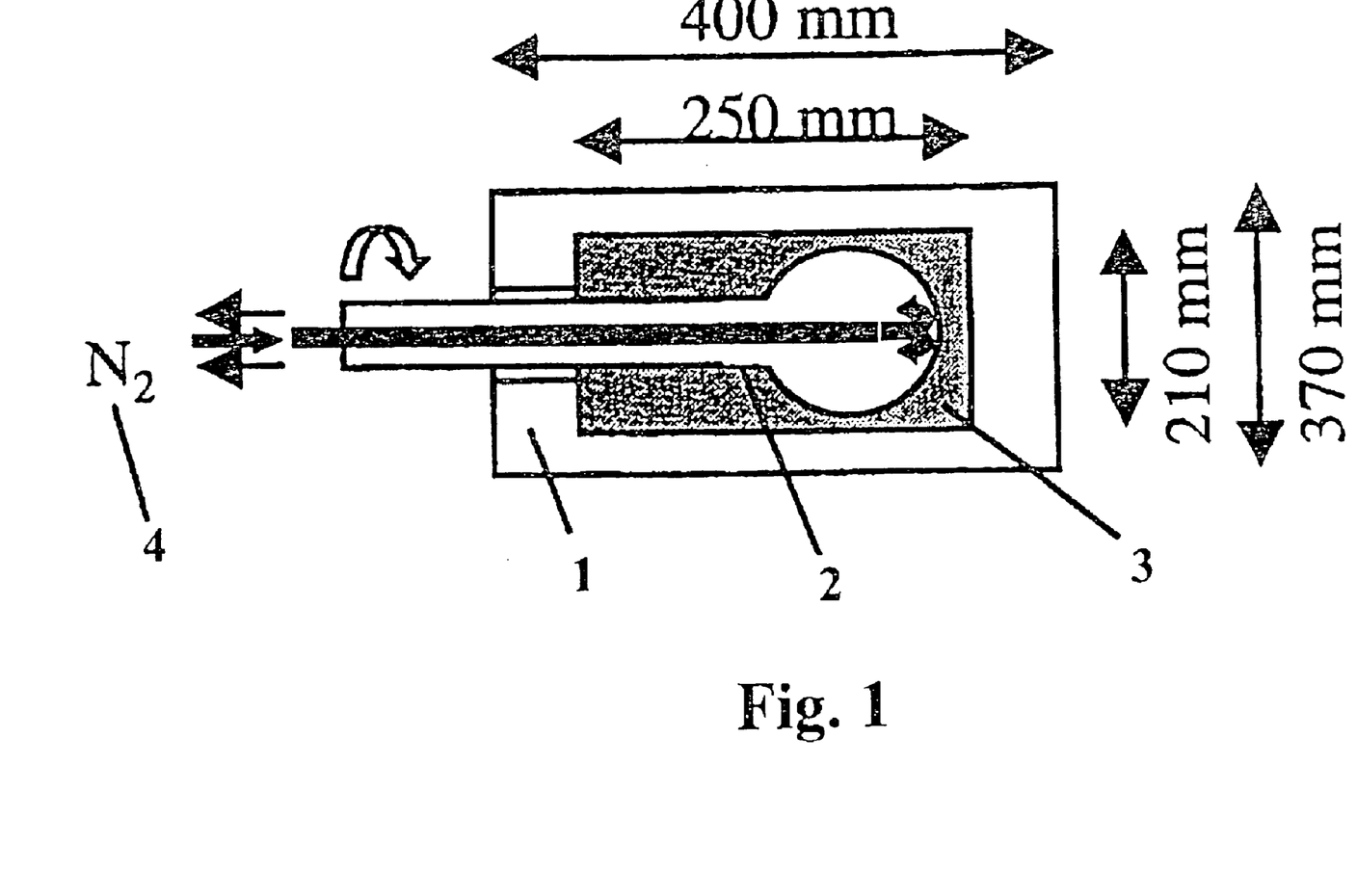

The mixture obtained was dried in a spray drier (apparatus from Niro, DE, $T^{in}=350°$ C., $T^{out}=105°$ C.). 150 g of the resulting solid were heated from 25° C. to 275° C. at a heating rate of 5° C./min in a rotary sphere oven according to FIG. 1 (quartz glass sphere having an internal volume of 1 liter; 1=oven housing, 2=rotating flask, 3=heated space, 4=nitrogen/air stream) under air (10 l/h). Immediately thereafter, heating was effected from 275° C. to 650° C. at a heating rate of 2° C./min under a stream of molecular nitrogen (10 l(S.T.P.)/h) and the mixture was kept at this temperature under the nitrogen stream for 6 hours. It was then left to cool to 25° C. while maintaining the nitrogen stream.

Figure 2:
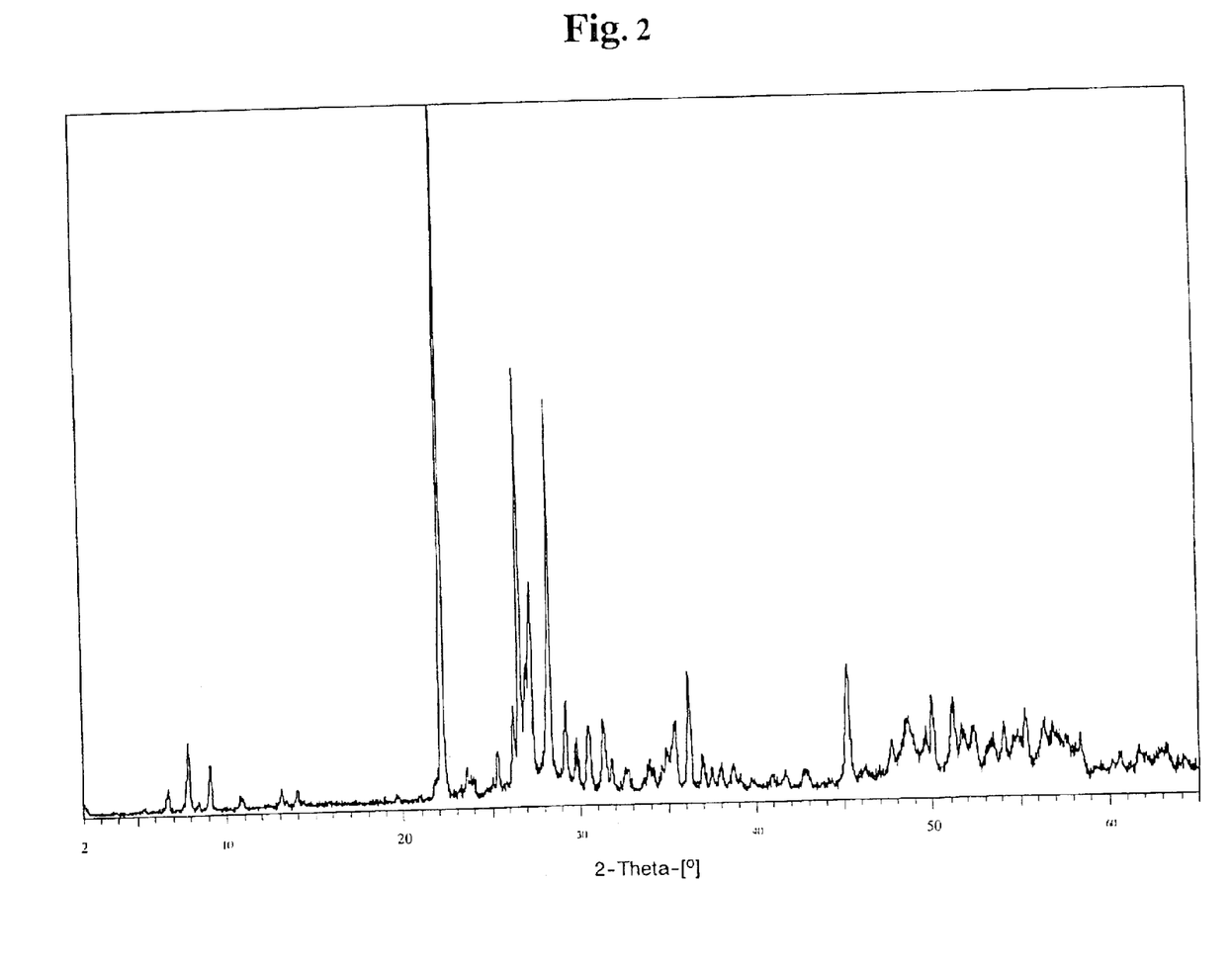

The calcined black material M had the chemical composition $Mo_{1.0}V_{0.33}Te_{0.14}Nb_{0.11}O_x$. The associated X-ray diffraction pattern is shown in FIG. 2. It shows a mixture of i-phase and k-phase. The ratio R is 0.35.

The calcined material was milled in a Retsch mill (centrifugal mill, type ZM 100, from Retsch, Germany) (particle size ≦ 0.12 mm).

75 g of the resulting powder were applied to 162 g of spherical supports having a diameter of 2.2–3.2 mm ($R_z$=45 µm, support material=steatite from Ceramtec, Germany, total pore volume of the support ≦1% by volume, based on the total support volume). For this purpose, the support was initially taken in a coating drum having an internal volume of 2 l (angle of inclination of the central axis of the drum relative to the horizontal=30°). The drum was rotated at 25 revolutions per minute. About 30 ml of a mixture of glycerol and water (glycerol:water weight ratio=1:3) was sprayed onto the support via an atomizer nozzle operated with 300 l(S.T.P.)/h of compressed air over 60 minutes. The nozzle was installed in such a way that the spray cone wet the supports transported in the drum by metal driver plates to the uppermost point of the inclined drum, in the upper half of the rolling zone. The finely divided active material powder was introduced into the drum via a powder screw, the point of addition of the powder being within the rolling zone or below the spray cone. By periodic repetition of wetting and powder metering, the support provided with the base coat itself became the support in the subsequent period.

After coating was complete, the coated support was dried for 16 hours at 120° C. in a through-circulation drying oven (from Binder, Germany, internal volume 53 l). Glycerol was removed by a subsequent two-hour heat treatment at 150° C. under air. A comparative coated catalyst Sa was obtained.

b) Comparison 128.0 g of ammonium metavanadate ($V_2O_5$ content of 77.4% by weight, ideal composition: $NH_4VO_3$, from G. f. E. Nürnberg) were dissolved at 80° C. in 2 925 ml of water in a stainless steel container. The resulting yellowish clear solution was cooled to 60° C. Thereafter, 304.5 g of telluric acid (99% by weight of $H_6TeO_6$, from Fluka) and 585.0 g of ammonium heptamolybdate (81.53% by weight of $MoO_3$, from Starck, ideal composition: $(NH_4)_6Mo_7O_{24} \cdot 4H_2O$) were added in succession to this solution while stirring and while maintaining the 60° C. The resulting deep red solution A was cooled to 30° C. Separately therefrom, in a second stainless steel container, 69.6 g of niobic acid (Nb content 48.6% by weight, from Starck), together with 343.5 g of oxalic acid dihydrate, were dissolved at 60° C. in 750 ml of water. The resulting solution B was cooled to 30° C. The solutions A and B were combined at 30° C., the solution B being stirred into the solution A. The addition was effected over a period of 3 minutes. An orange-red suspension formed. This suspension was then spray-dried (spray tower from Nipolosa; the temperature of the receiver was kept at 30° C., $T^{in}=330°$ C., $T^{out}=110°$ C.; duration of drying: 2 h). The resulting spray-dried material was a homogeneous olive-green powder.

Figure 3:
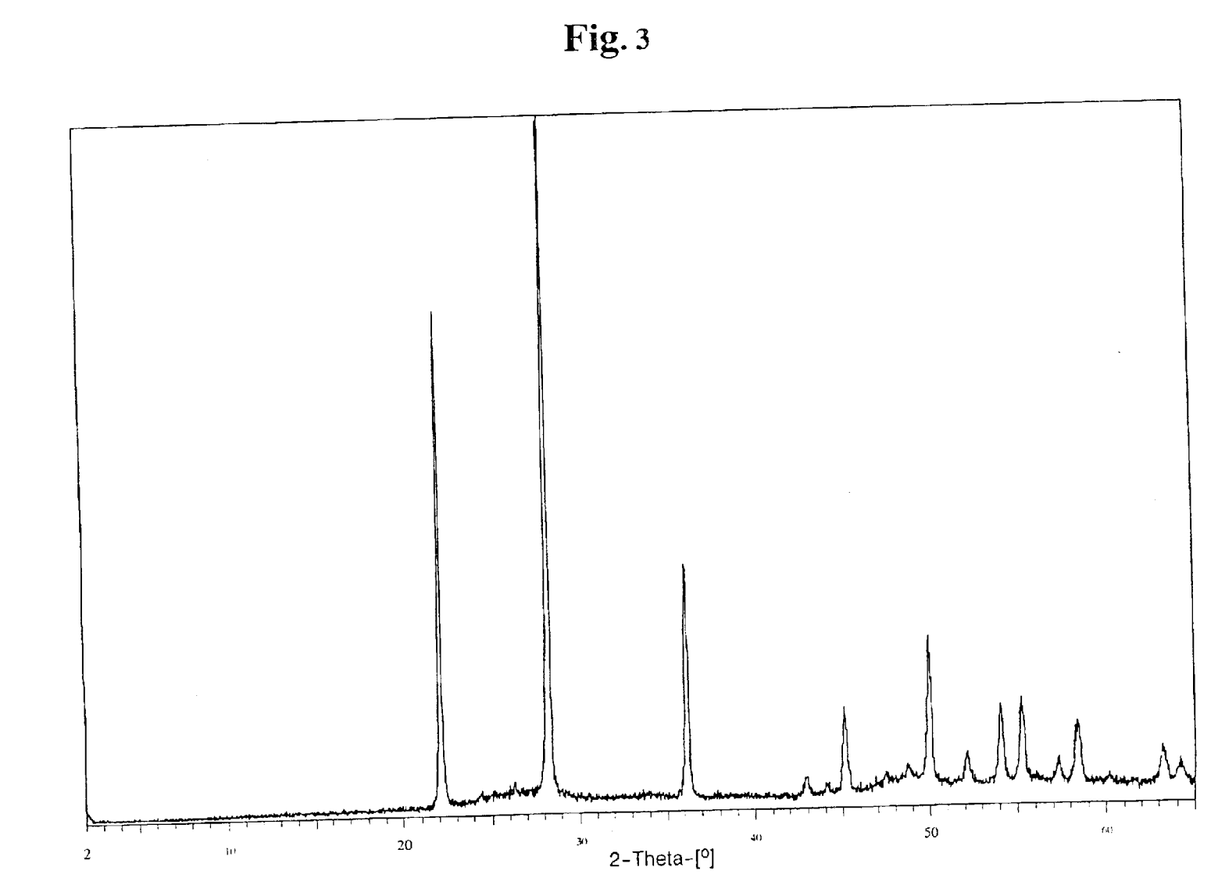

100 g of the spray-dried powder were calcined in a rotary sphere oven according to FIG. 1. For this purpose, heating was first effected linearly in the course of 27.5 minutes, under an air stream of 50 l(S.T.P.)/h, from 25° C. to 275° C. and this temperature was maintained for 1 hour while maintaining the air stream. Thereafter, the air stream was replaced by a nitrogen stream of 50 l(S.T.P.)/h and heating was effected in the course of 32.5 minutes linearly from 275° C. to 600° C. This temperature and the nitrogen stream were maintained for 2 hours. Finally, cooling to 25° C. was effected by leaving to stand while maintaining the nitrogen stream. The calcined material was then milled in a Retsch mill (centrifugal mill, type ZM 100, from Retsch, Germany) (particle size ≦ 0.12 mm). A black powder having the chemical composition $Mo_{1.0}V_{0.33}Te_{0.41}Nb_{0.11}O_x$ resulted. The associated X-ray diffraction pattern is shown in FIG. 3 (R=0). It shows substantially pure k-phase. A comparative coated catalyst Sb was prepared as in a) using 75 g of the powder.

c) According to the Invention

Figure 4:
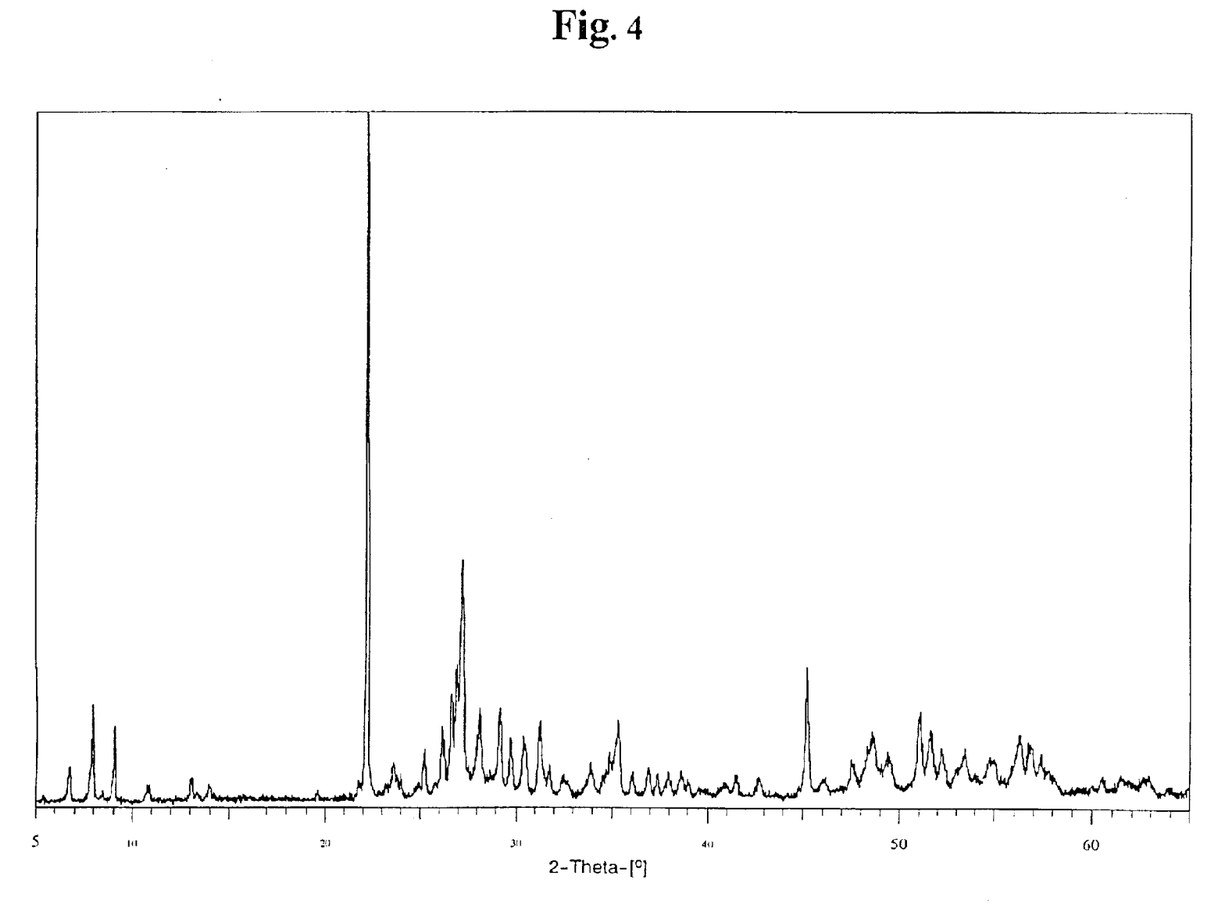

First, 230 g of the black calcined material M from a) were prepared. These were added at 70° C. to 2 300 g of a 10% strength by weight aqueous nitric acid ($HNO_3$) and the suspension obtained was stirred for 7 hours while maintaining the 70° C. Cooling to 25° C. was then effected. The solid present in the black suspension was separated from the aqueous phase by filtration, washed nitrate-free with water and then dried overnight in a through-circulation drying oven at 120° C. Of the 230 g used, 181.4 g (=78.7% by weight) remained after the treatment described above. Chemical analysis of the solid obtained gave the composition $Mo_1V_{0.26}Te_{0.09}Nb_{0.14}O_x$. The associated X-ray diffraction pattern is shown in FIG. 4. It shows exclusively i-phase. The ratio R is 0.74.

The dried material was then milled as in a) in a Retsch mill (particle size≦0.12 mm) and was processed as in a) to give a coated catalyst Sc to be used according to the invention.

d) According to the Invention

Figure 5:
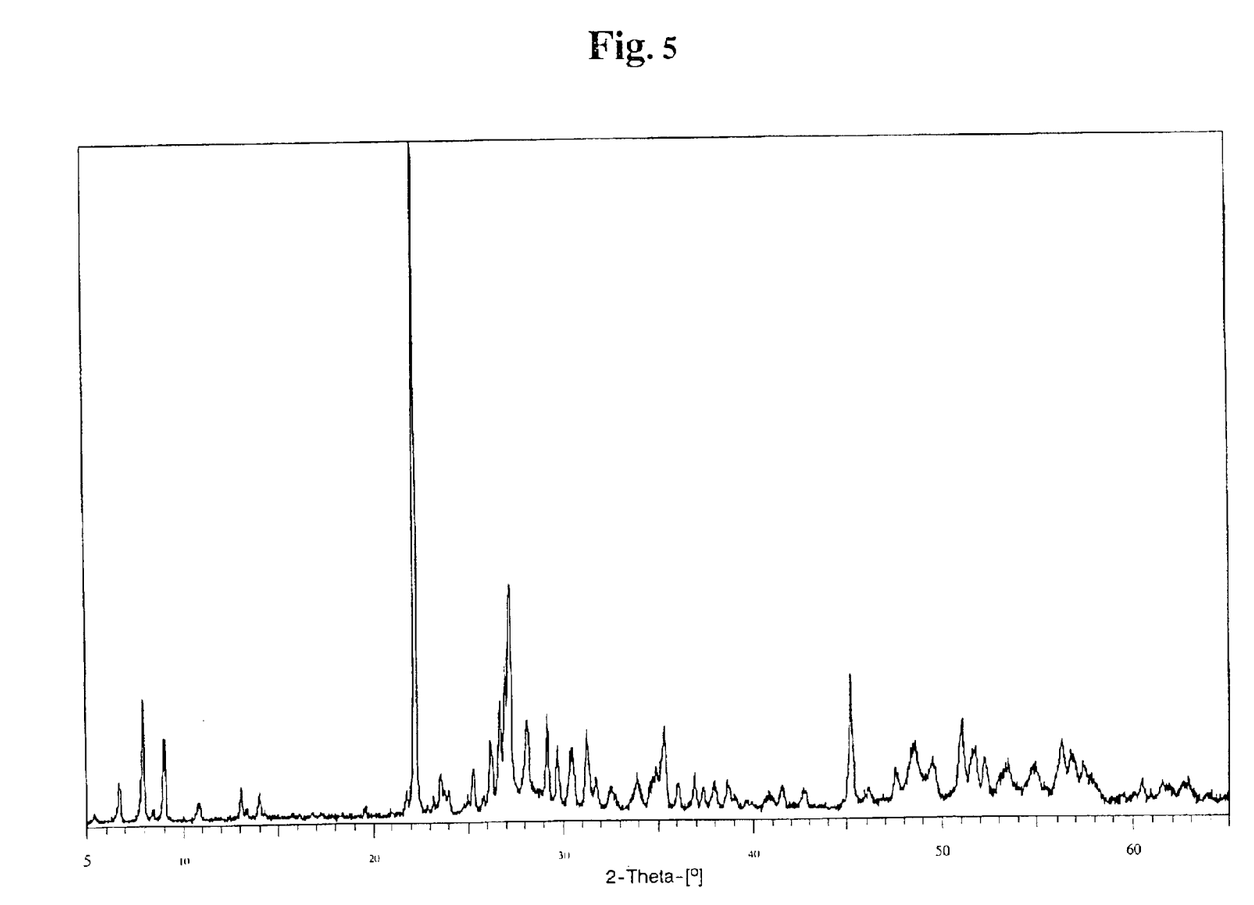

A coated catalyst Sd was prepared as described under c). Instead of 10% strength by weight aqueous nitric acid, however, a 20% strength by weight aqueous nitric acid was used. The associated X-ray diffraction pattern is shown in FIG. 5. It shows exclusively i-phase. The ratio R is 0.74.

e) According to the Invention

Figure 6:
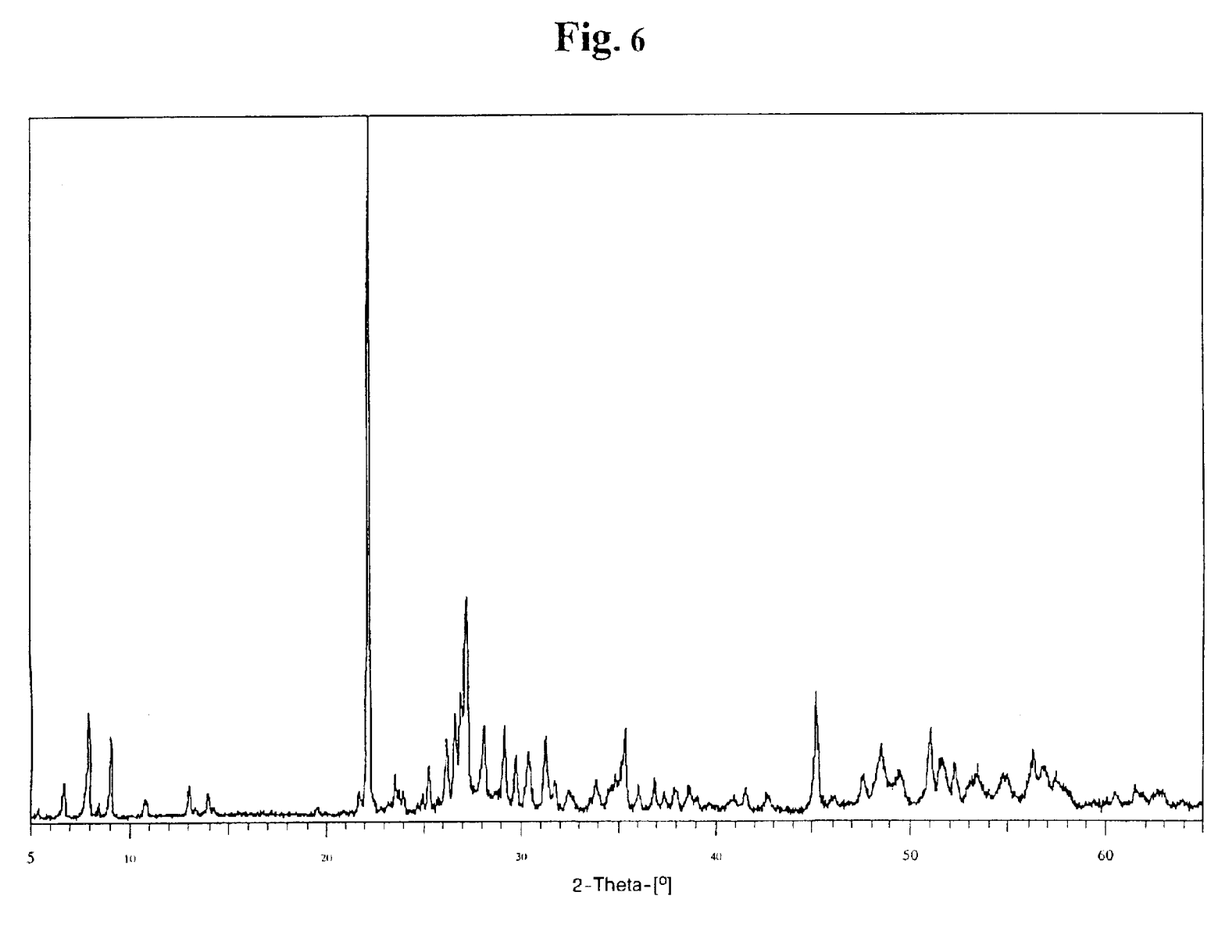

A coated catalyst Se was prepared as described under c). Instead of 10% strength by weight aqueous nitric acid, however, a 30% strength by weight aqueous nitric acid was used. The associated X-ray diffraction pattern is shown in FIG. 6. It shows exclusively i-phase. The ratio R is 0.73.

B) Testing of the Catalysts

A V2A stainless steel reaction tube (length=140 cm, external diameter=60 mm, internal diameter=8.5 mm) was loaded with each of the coated catalysts from A). The loading length was chosen as 52 cm. A preliminary 30 cm long bed of steatite beads (diameter: 2.2–3.2 mm, Ceramtec) served for warming up the reaction gas starting mixture. The reaction tube was finally filled with the same steatite beads after the catalyst zone. The reaction tube was heated from the outside over its entire length by means of electrical heating mats. The mat temperature was chosen at 340° C. The reaction was carried out at a pressure of 2 bar absolute and with a residence time (based on the catalyst bed) of 2.4 seconds using a feed (reaction gas starting mixture) having the molar composition propane:air:water=1:15:14. The results listed in the table were obtained depending on the coated catalyst used. C[mol %]=propane conversion in a single pass through the reaction tube. S[mol %]=selectivity with respect to the acrylic acid formation in a single pass through the reaction tube.

TABLE

| Coated catalyst | C [mol %] | S [mol %] |
|---|---|---|
| Sa | 12 | 40 |
| Sb | 5 | 12 |
| Sc | 18 | 69 |
| Sd | 28 | 72 |
| Se | 24 | 67 |

We claim:

1. A process comprising
   contacting a gaseous mixture comprising propane and oxygen with a catalyst to heterogeneously catalyze the oxidation of propane to acrylic acid,
   wherein the catalyst is at least one multimetal oxide material having stoichiometry I, $$Mo_1V_bM_c^1M_d^2O_n \quad (I),$$

where
   $M^1$ is Te, Sb, or both Sb and Te,
   $M^2$ is at least one element selected from the group consisting of Nb, Ta, W, Ti, Al, Zr, Cr, Mn, Ga, Fe, Ru, Go, Rh, Ni, Pd, Pt, La, Bi, B, Ce, Sn, Zn, Si and In,
   b is from 0.01 to 1,
   c is from >0 to 1,
   d is from >0 to 1 and
   n is a number which is determined by the valency and frequency of the elements other than oxygen in (I),
   wherein the X-ray diffraction pattern of the multimetal oxide material has reflections h, i and k whose peaks are at the diffraction angles (2θ): 22.2±0.4° (h), 27.3±0.4° (i) and 28.2±0.4° (k),
   the reflection h is the most intense reflection within the X-ray diffraction pattern and has a half-width of not more than 0.5°,
   the intensity $P_i$ of the reflection i and the intensity $P_k$ of the reflection k satisfy the relationship 0.65≦R≦0.85, where R is the intensity ratio defined by the formula $$R=P_i/(P_i+P_k)$$

and
   the half-width of the reflection i and the reflection k each are ≦1°, wherein the at least one multimetal oxide material (I) has an X-ray diffraction pattern having no reflection with the peak position (2θ): 50.0±0.3°.

2. The process as claimed in claim 1, wherein $M^1$ is Te.
3. The process as claimed in claim 1, wherein $M^2$ is Nb.
4. The process as claimed in claim 1, wherein b is from 0.1 to 0.6.
5. The process as claimed in claim 1, wherein c is from 0.01 to 1.
6. The process as claimed in claim 1, wherein d is from 0.01 to 1.
7. The process as claimed in claim 1, wherein 0.67≦R≦0.75.
8. The process as claimed in claim 1, wherein R is from 0.70 to 0.75.
9. The process as claimed in claim 1, which is carried out in a fluidized bed.
10. The process as claimed in claim 1, wherein R is 0.72.
11. The process as claimed in claim 1, wherein the X-ray diffraction pattern of the multimetal oxide material has at least one further reflection at one or more of the following diffraction angles (2θ): 9.0±0.4° (l), 6.7±0.4° (o), or 7.9±0.4° (p).
12. The process as claimed in claim 1, wherein the X-ray diffraction pattern of the multimetal oxide material has a further reflection at a diffraction angle (2θ): 45.2±0.4° (q).
13. The process as claimed in claim 1, wherein the X-ray diffraction pattern of the multimetal oxide material has a reflections at (2θ): 29.2±0.4° (m) and 35.4±0.4° (n).
14. The process as claimed in claim 1, wherein the gaseous mixture further comprises steam.
15. The process as claimed in claim 1, wherein the gaseous mixture comprises from 1 to 7% by volume of propane, from 44 to 99 % by volume of air, and from 0 to 55% by volume of steam.
16. The process as claimed in claim 1, further comprising separating the acrylic acid from unconverted propane and further contacting the unconverted propane with the catalyst.
17. The process as claimed in claim 1, wherein the catalyst is a multimetal oxide material having the following stoichiometry:

$$Mo_1V_{0.26}Te_{0.09}Nb_{0.14}O_x.$$

18. The process as claimed in claim 1, wherein the catalyst is coated on a support.

19. The process as claimed in claim 1, wherein c and d are from 0.01 to 1.

20. The process as claimed in claim 1, wherein c is from 0.05 to 0.4.

21. The process as claimed in claim 1, wherein d is from 0.1 to 0.6.

22. The process as claimed in claim 1, wherein b is from 0.1 to 0.6, c is from 0.05 to 0.4 and d is from 0.1 to 0.6.

23. The process as claimed in claim 1, wherein the gaseous mixture comprises from 70 to 95% by volume of propane, from 5 to 30% by volume of molecular oxygen and from 0 to 25% by volume of steam.

24. The process as claimed in claim 1, wherein the multimetal oxide material is obtained by first producing a multimetal oxide material having both the i-phase and other phases then removing other phases.

25. The process as claimed in claim 24, wherein other phases are removed by washing with a liquid.

26. The process as claimed in claim 25, wherein the liquid is at least one selected from the group consisting of an aqueous solution of an organic acid, an aqueous solution of an inorganic acid, an alcohol, and an aqueous hydrogen peroxide solution.

27. The process as claimed in claim 26, wherein the liquid is an aqueous solution of an organic or inorganic acid, the organic acid is at least one selected from the group consisting of oxalic, formic, acetic, citric and tartaric acid, and the inorganic acid is nitric acid.

28. The process as claimed in claim 18, wherein the longest dimension of the support is from 1 to 10 mm.

29. The process as claimed in claim 28, wherein the support is a ring or a sphere.

30. The process as claimed in claim 18, wherein the thickness of the catalyst coating on the support is from 10 to 1,000 $\mu$m.

* * * * *

UNITED STATES PATENT AND TRADEMARK OFFICE
CERTIFICATE OF CORRECTION

PATENT NO. : 6,867,328 B2  
DATED : March 15, 2005  
INVENTOR(S) : Borgmeier et al.

It is certified that error appears in the above-identified patent and that said Letters Patent is hereby corrected as shown below:

<u>Title page,</u>
Items [45] and [*] Notice, should read
-- [45] **Date of Patent: *Mar. 15, 2005**

[*] Notice: Subject to any disclaimer, the term of this patent is extended or adjusted under 35 U.S.C. 154(b) by 0 days.

This Patent is subject to a terminal disclaimer. --

Signed and Sealed this

Twenty-fourth Day of May, 2005

JON W. DUDAS
*Director of the United States Patent and Trademark Office*